US012754175B2

(12) United States Patent
Choi et al.

(10) Patent No.: US 12,754,175 B2
(45) Date of Patent: Oct. 6, 2026

(54) ARTIFICIAL INTELLIGENCE APPARATUS FOR DETECTING TARGET GAS IN SMALL SAMPLE DOMAIN AND OPERATING METHOD THEREOF

(71) Applicant: ELECTRONICS AND TELECOMMUNICATIONS RESEARCH INSTITUTE, Daejeon (KR)

(72) Inventors: Jae Hun Choi, Daejeon (KR); Do Hyeun Kim, Daejeon (KR); Hwin Dol Park, Daejeon (KR); Seunghwan Kim, Daejeon (KR); Hyung Wook Noh, Daejeon (KR); Chang-Geun Ahn, Daejeon (KR); YongWon Jang, Daejeon (KR); Kwang Hyo Chung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 384 days.

(21) Appl. No.: 18/509,735

(22) Filed: Nov. 15, 2023

(65) Prior Publication Data

US 2024/0192187 A1 Jun. 13, 2024

(30) Foreign Application Priority Data

Dec. 12, 2022 (KR) ........................ 10-2022-0173132
Mar. 27, 2023 (KR) ........................ 10-2023-0039845

(51) Int. Cl.
*G01N 33/00* (2006.01)

(52) U.S. Cl.
CPC ..... *G01N 33/0034* (2013.01); *G01N 33/0011* (2013.01); *G01N 33/0062* (2013.01); *G01N 33/0019* (2024.05)

(58) Field of Classification Search
CPC ........... G01N 33/0034; G01N 33/0011; G01N 33/0062; G01N 33/0019; G01N 33/0031
See application file for complete search history.

(56) References Cited

U.S. PATENT DOCUMENTS 10,176,427 B2 * 1/2019 Dubey .................. G06F 16/185
10,438,012 B2 * 10/2019 Finkel .................... G06Q 50/06
(Continued)

FOREIGN PATENT DOCUMENTS

CN 106124700 A 11/2016
KR 101720570 B1 3/2017
(Continued)

OTHER PUBLICATIONS

Yuelin Zhang et al,"TDACNN: Target-domain-free domain adaptation convolutional ne-ural network for drift compensation in gas sensors", Sensors & Actuators: B. Chemical 361 (2022) 131739, Mar. 19, 2022.
(Continued)

*Primary Examiner* — Tung S Lau
(74) *Attorney, Agent, or Firm* — Rabin & Berdo, P.C.

(57) ABSTRACT

Disclosed is an artificial intelligence apparatus for detecting a target gas, which includes a mixed gas measurement unit that measures a mixed gas collected in a plurality of domains through a sensor array to generate sensing data including heterogeneous domain measurement data measured from the mixed gas collected in a domain different from the target gas and target domain measurement data measured from the mixed gas collected from the same domain as the target gas, a heterogeneous intelligence model deep learning unit that receives the heterogeneous domain measurement data to train a heterogeneous intelligence model, a target intelligence model deep learning unit that receives the heterogeneous intelligence model and the target domain measurement data to train a target intelligence model, and a target
(Continued)

gas detection unit that determines whether an environmental gas includes the target gas using the target intelligence model.

9 Claims, 7 Drawing Sheets

(56) References Cited

U.S. PATENT DOCUMENTS

| | | | |
|---|---|---|---|
| 11,747,314 | B2 | 9/2023 | Choi et al. |
| 2021/0201152 | A1 | 7/2021 | Santillán Perez et al. |
| 2022/0170900 | A1 | 6/2022 | Choi et al. |
| 2022/0187262 | A1 | 6/2022 | Jang et al. |

FOREIGN PATENT DOCUMENTS

| | | | | |
|---|---|---|---|---|
| KR | 102077038 | B1 | 2/2020 | |
| KR | 20220077972 | A | 6/2022 | |
| WO | WO 2022145812 | A1 * | 7/2022 | ......... B01D 53/8625 |

OTHER PUBLICATIONS

Lu Han et al., "A New Method of Mixed Gas Identification Based on a Convolutional Neural Network for Time Series Classification", Sensors, Apr. 26, 2019, 19, 1960, pp. 1-23.

* cited by examiner

ARTIFICIAL INTELLIGENCE APPARATUS FOR DETECTING TARGET GAS IN SMALL SAMPLE DOMAIN AND OPERATING METHOD THEREOF

CROSS-REFERENCE TO RELATED APPLICATIONS

This application claims priority under 35 U.S.C. § 119 to Korean Patent Application Nos. 10-2022-0173132 filed on Dec. 12, 2022, and 10-2023-0039845 filed on Mar. 27, 2023, respectively, in the Korean Intellectual Property Office, the disclosures of which are incorporated by reference herein in their entireties.

BACKGROUND

Embodiments of the present disclosure described herein relate to an artificial intelligence apparatus, and more particularly, relate to an artificial intelligence apparatus capable of detecting a target gas in a small sample domain, and a method of operating the same.

Olfactory intelligence is a technology that mimics the human sense of smell through sensor arrays, sensing data, and artificial intelligence that may detect target gases. The electronic nose is a product of olfactory intelligence, and the concept of the olfactory intelligence is established by Gardner and Bartlett in 1988. Unlike Gas chromatography (GC), Mass spectrometer (MS), Infrared Spectrometers (IRS), and Ion Mobility Spectrometers (IMS), which identify gases by measuring their physical quantities, the electronic nose implemented with the olfactory intelligence senses single or complex gases through a sensor array with low selectivity and high sensitivity, and detects target gases by training the sensed data through artificial intelligence.

Metal oxide semiconductor sensors (MOS) using metal catalysts are widely used with respect to $SnO_2$, $ZnO$, $In_2O_3$, $WO_3$, etc., which have high sensitivity as sensors that implement the sensor array, and have a method of measuring the change in electrical resistance when the target gas reacts with oxygen. Since the MOS sensor reacts to gases other than the target gas, the selectivity for specific gases is low.

Electrochemical Sensors (ECS) having relatively high selectivity with respect to specific gases compared to the MOS sensors are also widely used as the sensors that implement the sensor array. The ECS measure gas concentration using the current generated at a reaction electrode and a counter electrode when the target gas undergoes an oxidation reaction or a reduction reaction on surfaces of built-in electrodes. Even though the target gases are the same, when the concentrations are different, the amount of current between the two electrodes is measured differently.

Photoionization Detector Sensors (PIDS) measure the current that changes depending on the degree of ionization of the target gas, which is separated into negative ions and positive ions by UV light. Since the PIDS are suitable for measuring volatile organic compounds (VOCs) and have excellent precision, the PIDS are currently most widely used as portable and installed gas meters. In addition, the sensor array may be implemented through various sensors, and the sensor array should be composed of sensors with characteristics suitable for domains. The characteristics of the used sensors are illustrated in Table 1 below.

TABLE 1

| Sensor type | Applicable domain | Strength | Weakness |
|---|---|---|---|
| Metal Oxide Sensor | Grocery, Food, Cosmetics, Air environment | Oxidation/reduction gas detection, Low cost, High sensitivity, Long life, Fast speed, Convenience, Robustness, Ultra-compactness | Low selectivity, Temperature rise, Sulfur poisoning, Low linearity, Humidity sensitivity |
| Conducting polymer | Medical treatment, Pharmaceutical, Food, Beverage, Air environment | Oxidation/reduction gas detection, Room temperature operation, Convenience, Fast speed | Humidity/temperature sensitivity, Short lifespan |
| Electrochemical Sensors | Safety, Medical treatment, Air environment | Low power, Linearity, Temperature maintenance, High selectivity | Volume, Low sensitivity, Short lifespan |
| Photoionization Detector Sensors | Medical treatment | High sensitivity, Linearity | Complexity |

Sensing data measured through a sensor array has time-series characteristics depending on the sampling interval. Due to the physical characteristics of the sensor, the sampling values increase from an initial value to a specific value, maintain the specific value, and then decrease back to the initial value. Among the sensors that make up the sensor array, there are sensors with high reactivity and sensors with low reactivity with respect to the target gas, and a reaction speed is also different for each sensor. Therefore, the sampling interval should be adjusted to better reflect reactivity and reaction speed characteristics.

Sensor arrays are used in open or closed environments, and in these environments, it is common for one or more gases to be mixed. Therefore, a role of the sensor array is to detect whether an environmental gas contains the target gas. Since artificial intelligence for target gas detection is trained through sensing data, the configuration of the sensor array is particularly important. In general, the accuracy of artificial intelligence trained through sensing data may be increased when a sensor array is composed of sensors that have high reactivity with respect to the target gas among the mixed gases and have low reactivity with respect to gases other than the target gas among the mixed gases.

To learn artificial intelligence to accurately detect the target gas, a lot of sensing data measured in various situations is required. To secure such sensing data for training, many gases in various environments should be measured. In addition, data obtained by various organizations may be integrated and used, but since the configuration of the sensor array may be different for each organization, it is difficult to use the data directly for training. As another method, a sample gas for training may be created by mixing the target gas with various types of environmental gases. In this case, there is an advantage in that data similar to data obtained by measuring actual environmental gases may be collected.

When a lot of sample gas for training is generated, artificial intelligence for detecting target gases may be trained more accurately. For training, traditional machine learning (support vector machine (SVM), decision tree, etc.) algorithm, deep learning (DNN, CNN, RNN, LSTM, ResNet, Transformers, etc.) algorithm, reinforcement learning (SARSA, DQN, A2C, TRPO, SAC, etc.) algorithm may be used. However, to generate sample gases for training, various environmental gases and a large amount of target gas are required. In this case, securing a large amount of target gas is problematic, especially when generating sample gas for training that contains drugs, explosives, and toxic gases, so it is difficult to secure a large amount of drugs, explosives, and toxic gases. Therefore, a method for accurately training artificial intelligence for target gas detection in a domain with few samples is required.

SUMMARY

Embodiments of the present disclosure provide an artificial intelligence apparatus capable of accurately training an artificial intelligence for detecting a target gas in a domain with few samples where it is difficult to secure a large amount of target gas, and a method of operating the same According to an embodiment of the present disclosure, an artificial intelligence apparatus for detecting a target gas, includes a mixed gas measurement unit that measures a mixed gas collected in a plurality of domains through a sensor array to generate sensing data including heterogeneous domain measurement data measured from the mixed gas collected in a domain different from the target gas and target domain measurement data measured from the mixed gas collected from the same domain as the target gas, a heterogeneous intelligence model deep learning unit that receives the heterogeneous domain measurement data to train a heterogeneous intelligence model, a target intelligence model deep learning unit that receives the heterogeneous intelligence model and the target domain measurement data to train a target intelligence model, and a target gas detection unit that determines whether an environmental gas includes the target gas using the target intelligence model.

According to an embodiment of the present disclosure, a method of operating an artificial intelligence apparatus for detecting target gas includes measuring a mixed gas collected in a plurality of domains through a sensor array and generating sensing data including heterogeneous domain measurement data measured from the mixed gas collected in a domain different from the target gas and target domain measurement data measured from the mixed gas collected from the same domain as the target gas, receiving the heterogeneous domain measurement data and training a heterogeneous intelligence model, receiving the heterogeneous intelligence model and the target domain measurement data and training a target intelligence model, and determining whether an environmental gas includes the target gas using the target intelligence model.

According to an embodiment of the present disclosure, a non-transitory computer-readable medium includes a program code that, when executed by a processor, causes the processor to measure a mixed gas collected in a plurality of domains through a sensor array to generate sensing data including heterogeneous domain measurement data measured from the mixed gas collected in a domain different from the target gas and target domain measurement data measured from the mixed gas collected from the same domain as the target gas, to receive the heterogeneous domain measurement data to train a heterogeneous intelligence model, to receive the heterogeneous intelligence model and the target domain measurement data to train a target intelligence model, and to determine whether an environmental gas includes the target gas using the target intelligence model.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described in detail and clearly to such an extent that an ordinary one in the art easily implements the present disclosure.

Components that are described in the detailed description with reference to the terms "unit", "module", "block", "~er or ~or", etc. and function blocks illustrated in drawings will be implemented with software, hardware, or a combination thereof. For example, the software may be a machine code, firmware, an embedded code, and application software. For example, the hardware may include an electrical circuit, an electronic circuit, a processor, a computer, an integrated circuit, integrated circuit cores, a pressure sensor, an inertial sensor, a microelectromechanical system (MEMS), a passive element, or a combination thereof.

Figure 1:
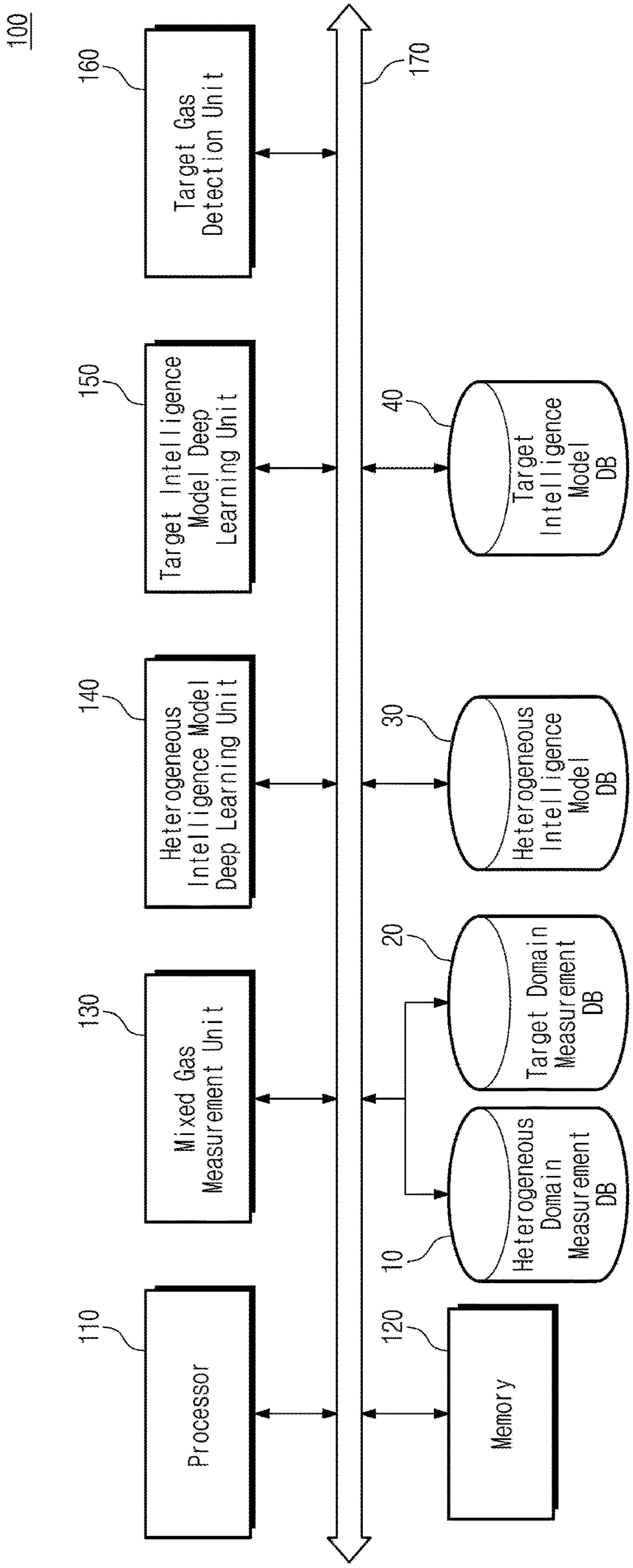
FIG. 1 is a block diagram illustrating an artificial intelligence apparatus for detecting a target gas in a small sample domain, according to an embodiment of the present disclosure.

FIG. 1 is a block diagram illustrating an artificial intelligence apparatus 100 for detecting a target gas in a small sample domain, according to an embodiment of the present disclosure. The artificial intelligence apparatus 100 may measure mixed gas through a sensor array. In this case, measurement data from the same domain as the target gas will be referred to as heterogeneous domain measurement data, and measurement data from a domain different from the target gas will be referred to as target domain measurement data. The artificial intelligence apparatus 100 may train a heterogeneous intelligence model using heterogeneous domain measurement data, may train a target intelligence model using the trained heterogeneous intelligence model and target domain measurement data, and then may detect whether an environmental gas contains the target gas by measuring the environmental gas collected in the actual environment. Referring to FIG. 1, the artificial intelligence apparatus 100 may include a processor 110, a memory 120, a mixed gas measurement unit 130, a heterogeneous intelligence model deep learning unit 140, a target intelligence model deep learning unit 150, a target gas detection unit 160, and a data bus 170. In addition, inside or outside the artificial intelligence apparatus 100, a heterogeneous domain measurement database (DB) 10 and a target domain measurement DB 20 for storing heterogeneous domain measurement data and target domain measurement data may be implemented, and a heterogeneous intelligence model DB 30 and a target intelligence model DB 40 for storing a heterogeneous intelligence model and a target intelligence model may be implemented.

The processor 110 may drive an artificial intelligence algorithm (e.g., an artificial intelligence algorithm used to train a heterogeneous intelligence model and a target intelligence model) used in the artificial intelligence apparatus 100, and the memory 120 may store and manage data generated while running an artificial intelligence algorithm and necessary commands and data. For example, the processor 110 may be combinational logic, sequential logic, one or more timers, counters, registers, state machines, one or more complex programmable logic devices (CPLDs), field programmable gate arrays (FPGAs), an application specific integrated circuit (ASIC), a central processing unit (CPU) such as complex instruction set computer (CSIC) processors such as x86 processors or a reduced instruction set computer (RISC) such as ARM processors, a graphics processing unit (GPU), a neural processing unit (NPU), a tensor processing unit (TPU), an accelerated processing unit (APU), etc., or a combination thereof, and the memory 120 may be a NAND flash memory, a flash memory such as a low-latency NAND flash memory, a persistent memory (PMEM) such as cross-grid non-volatile memory, a memory with large resistance changes, a phase change memory (PCM), etc., or a combination thereof, but the present disclosure is not limited thereto.

In addition, according to an embodiment, the above-described operations of the artificial intelligence apparatus 100 may be implemented with program codes stored in a non-transitory computer-readable medium. For example, the non-transitory computer-readable media may include magnetic media, optical media, or combinations thereof (e.g., a CD-ROM, a hard drive, a read-only memory, a flash drive, etc.).

The mixed gas measurement unit 130 may collect the mixed gas according to a certain protocol and may measure the collected gases through a sensor array. Among the measured gases, heterogeneous domain measurement data may be stored in the heterogeneous domain measurement DB 10, and target domain measurement data may be stored in the target domain measurement DB 20. The data stored in the heterogeneous domain measurement DB 10 may be used as data for training of the heterogeneous intelligence model deep learning unit 140, and the data stored in the target domain measurement DB 20 may be used as data for training the target intelligence model deep learning unit 150.

The heterogeneous intelligence model deep learning unit 140 may receive heterogeneous domain measurement data from the heterogeneous domain measurement DB 10 and may perform deep learning to train a heterogeneous intelligence model. The trained heterogeneous intelligence model may be stored in the heterogeneous intelligence model DB 30. The target intelligence model deep learning unit 150 may receive target domain measurement data from the target domain measurement DB 20 and may receive one or more heterogeneous intelligence models from the heterogeneous intelligence model DB 30 to train the target intelligence model. The trained target intelligence model may be stored in the target intelligence model DB 40. For example, the heterogeneous intelligence model deep learning unit 140 and the target intelligence model deep learning unit 150 may train a heterogeneous intelligence model and a target intelligence model using a model such as a CNN (Convolutional Neural Network), an LSTM (Long Short-Term Memory), an RNN (Recurrent Neural Network), a ResNet, etc., but the present disclosure is not limited thereto.

The target gas detection unit 160 may measure the environmental gas collected in the actual environment in the same manner as the mixed gas measurement unit 130, and may input the measured data into the target intelligence model to determine whether the environmental gas contains the target gas. The operations of the mixed gas measurement unit 130, the heterogeneous intelligence model deep learning unit 140, the target intelligence model deep learning unit 150, and the target gas detection unit 160 will be described in detail below with reference to FIGS. 2 to 7.

The data bus 170 may be a path along which data moves in the artificial intelligence apparatus 100. For example, the data bus 170 may transfer data between the heterogeneous domain measurement DB 10 and the target domain measurement DB 20 and the mixed gas measurement unit 130, data between the heterogeneous domain measurement DB 10 and the heterogeneous intelligence model deep learning unit 140, data between the heterogeneous intelligence model DB 30 and the heterogeneous intelligence model deep learning unit 140, data between the target domain measurement DB 20 and the heterogeneous intelligence model DB 30 and the target intelligence model deep learning unit 150, and data between the target intelligence model DB 40 and the target intelligence model deep learning unit 150.

Figure 2:
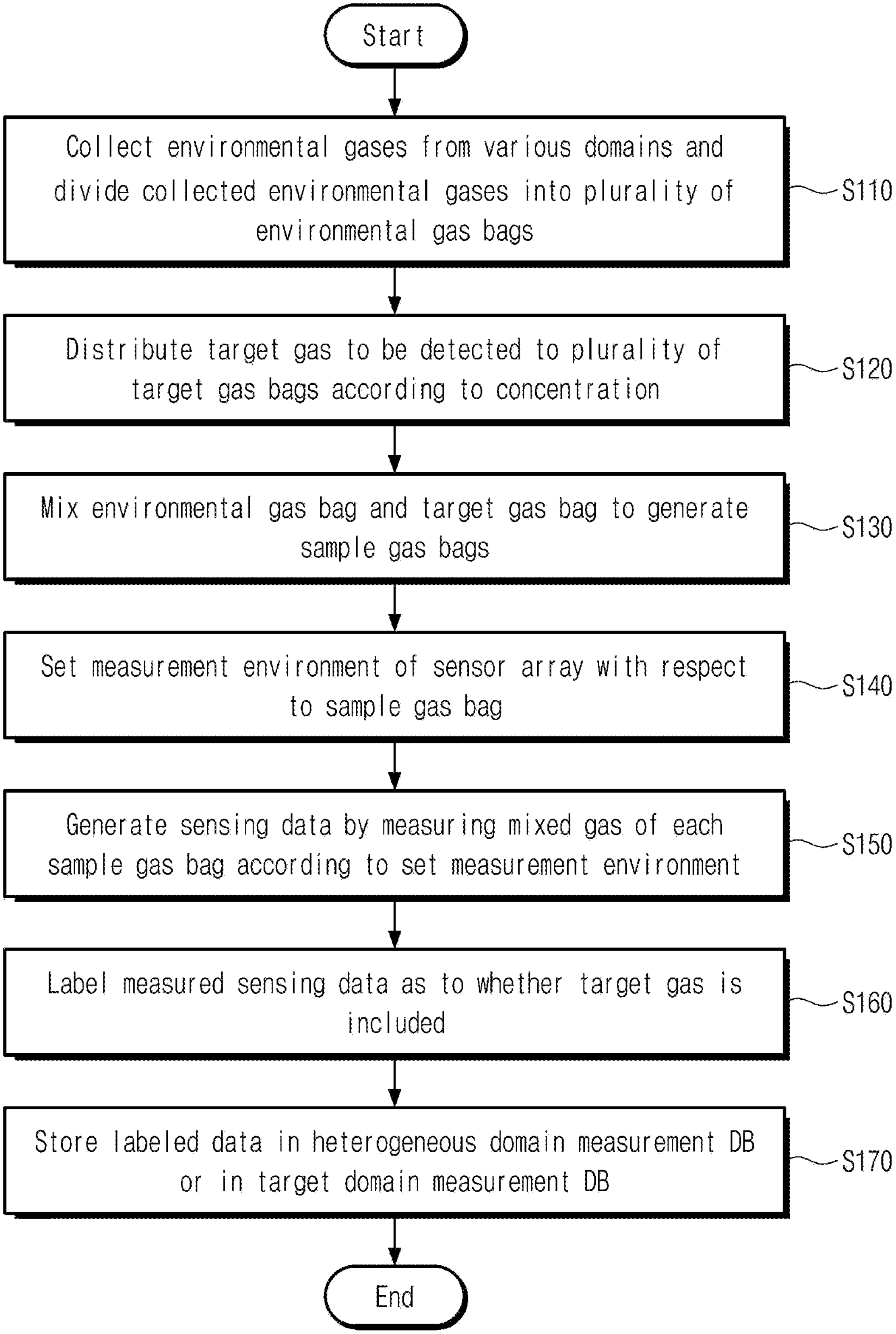
FIG. 2 is a flowchart illustrating an operation of a mixed gas measurement unit of FIG. 1.

FIG. 2 is a flowchart illustrating an operation of the mixed gas measurement unit 130 of FIG. 1. For example, the mixed gas measurement unit 130 may include a sensor array. Except that the number of samples for the target gas is small, the measurement method for heterogeneous domain measurement data is the same as the measurement method for target domain measurement data. To accurately train the target intelligence model for detecting a target gas without overfitting, the mixed gas containing a large amount of target gas should be collected from various domains. However, since in reality, domains in which a mixed gas containing a large amount of target gas may be collected are rare, the mixed gas measurement unit 130 according to an embodiment of the present disclosure uses a method of mixing target gases of various concentrations with respect to the mixed gases collected in several domains.

In detail, in operation S110, the mixed gas measurement unit 130 may collect environmental gases from various domains and may divide the collected environmental gases into a plurality of environmental gas bags. In this case, the number of environmental gas bags may be determined according to the capacity of gas required for measurement in the sensor array. In operation S120, the mixed gas measurement unit 130 distributes the target gas to be detected to a plurality of target gas bags according to concentration (e.g., 0%, 5%, 10%, 15%, etc.). For example, the number of target gas bags may be the same as the number of environmental gas bags.

In operation S130, the mixed gas measurement unit 130 may mix the environmental gas bag and the target gas bag at a 1:1 ratio to generate a plurality of sample gas bags for training artificial intelligence for detecting the target gas. In operation S140, the mixed gas measurement unit 130 may set the measurement environment of the sensor array with respect to the sample gas bag. For example, the measurement environment may be a combination of measurement temperature, gas pressure, sensor voltage, etc., and several types of measurement environments may be set with respect to one sample gas bag. The reason for setting up various measurement environments like this is because the physical and chemical characteristics of the sensors that make up the sensor array may change significantly depending on the environment, as a result, artificial intelligence for detecting the target gas may be trained using data corresponding to various environments.

In operation S150, the mixed gas measurement unit 130 may generate sensing data by measuring the mixed gas of each sample gas bag according to a set measurement environment. In operation S160, the mixed gas measurement unit 130 may label the measured sensing data as to whether the target gas is included. For example, the sensing data for a mixed gas with a target gas concentration of 0% may be labeled as "absence of target gas," and the sensing data for a mixed gas with a target gas concentration other than 0% may be labeled as "with target gas". In operation S170, the mixed gas measurement unit 130 may store sensing data (heterogeneous domain measurement data) from a domain different from the target gas among the sensing data in the heterogeneous domain measurement DB 10, and may store sensing data (target domain measurement data) from the same domain as the target gas among the sensing data in the target domain measurement DB 20.

Figure 3:
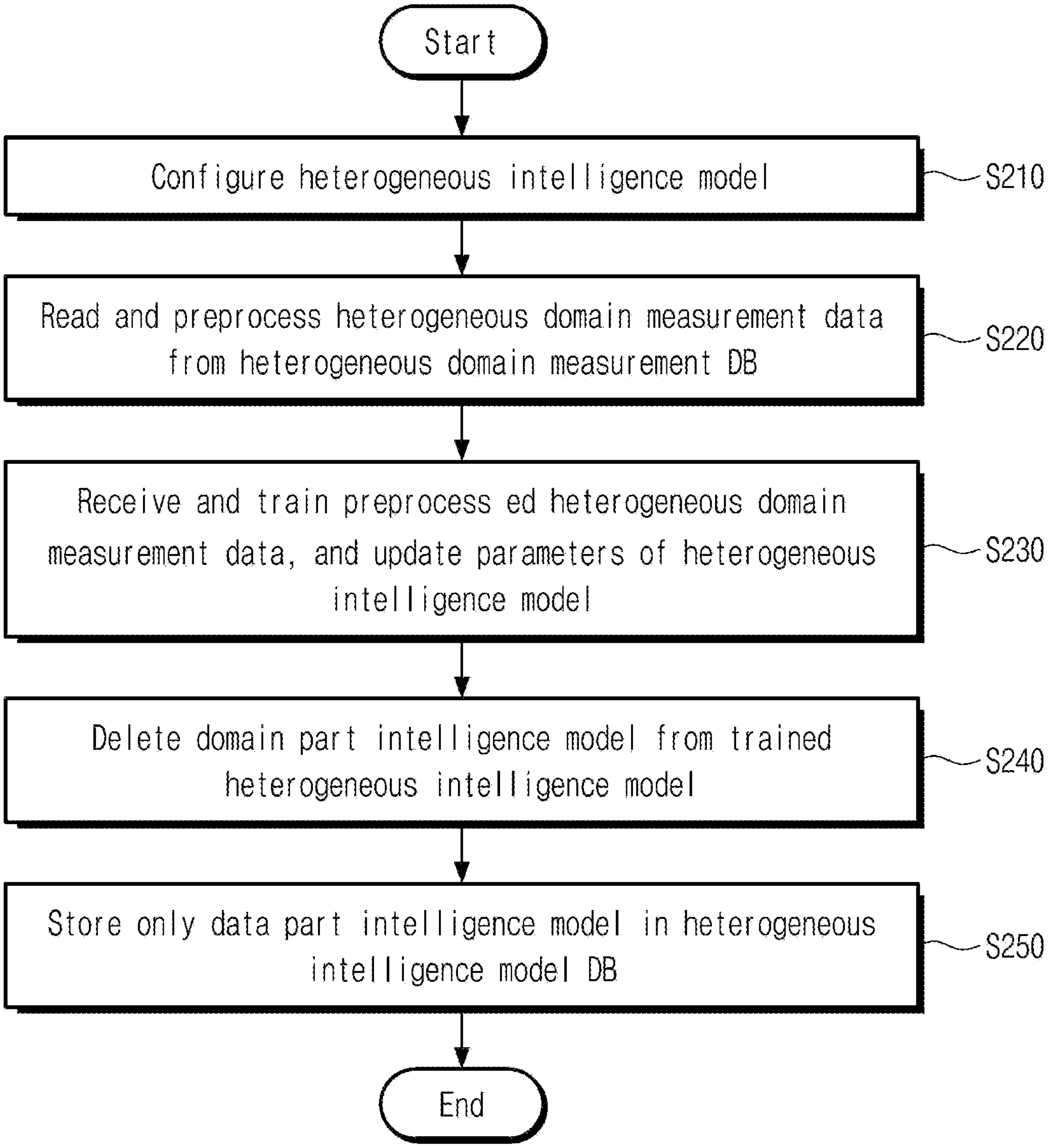
FIG. 3 is a flowchart illustrating an operation of a heterogeneous intelligence model deep learning unit of FIG. 1.
Figure 4:
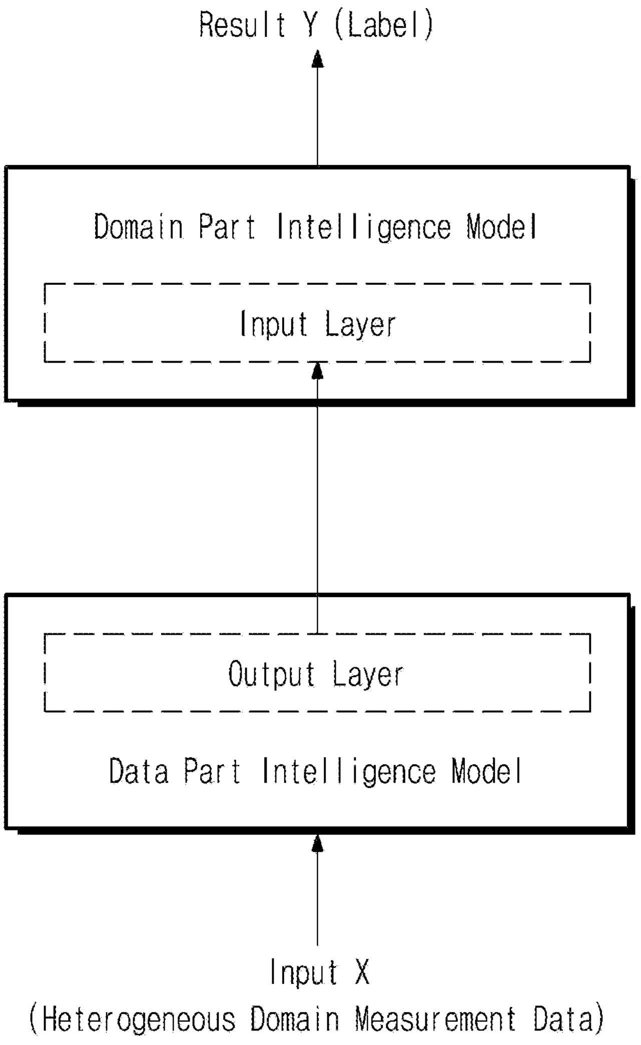
FIG. 4 illustrates a configuration of an intelligence model, according to an embodiment of the present disclosure.

FIG. 3 is a flowchart illustrating an operation of the heterogeneous intelligence model deep learning unit 140 of FIG. 1, and FIG. 4 illustrates a configuration of an intelligence model, according to an embodiment of the present disclosure. In operation S210, the heterogeneous intelligence model deep learning unit 140 may configure a heterogeneous intelligence model, and the heterogeneous intelligence model follows the configuration of the intelligence model illustrated in FIG. 4. Referring to FIG. 4, the intelligence model according to an embodiment of the present disclosure includes a data part intelligence model and a domain part intelligence model. The data part intelligence model is where sensing data measured from the sensor array is trained, the domain part intelligence model is where the characteristics of the domain to which the target gas belongs are trained, and an output layer of the data part intelligence model may be connected to an input layer of the domain part intelligence model. For example, in the case of heterogeneous intelligence models, the data part intelligence model may receive heterogeneous domain measurement data as input X, and the domain part intelligence model may output a label (with target gas or absence of target gas) as result Y.

Referring again to FIG. 3, in operation S220, the heterogeneous intelligence model deep learning unit 140 may read and preprocess heterogeneous domain measurement data from the heterogeneous domain measurement DB 10. For example, preprocessing may include handling missing values, removing outliers, normalizing data, etc. In operation S230, the heterogeneous intelligence model deep learning unit 140 may target the label "with target gas", may receive and train the preprocessed heterogeneous domain measurement data, and may update parameters (e.g., variables of the hidden layer) of the heterogeneous intelligence model.

In operation S240, the heterogeneous intelligence model deep learning unit 140 may delete the domain part intelligence model from the trained heterogeneous intelligence model. This is because a domain of the model trained from a current heterogeneous intelligence model is different from a domain of the target intelligence model to be trained in the future. However, since target domain measurement data and heterogeneous domain measurement data have similar properties to each other, the variables trained from the data part intelligence model may also be used in training the target intelligence model for detecting target gas. In operation S250, the heterogeneous intelligence model deep learning unit 140 may store only the data part intelligence model in the heterogeneous intelligence model DB 30 for future training of the target intelligence model.

Figure 5:
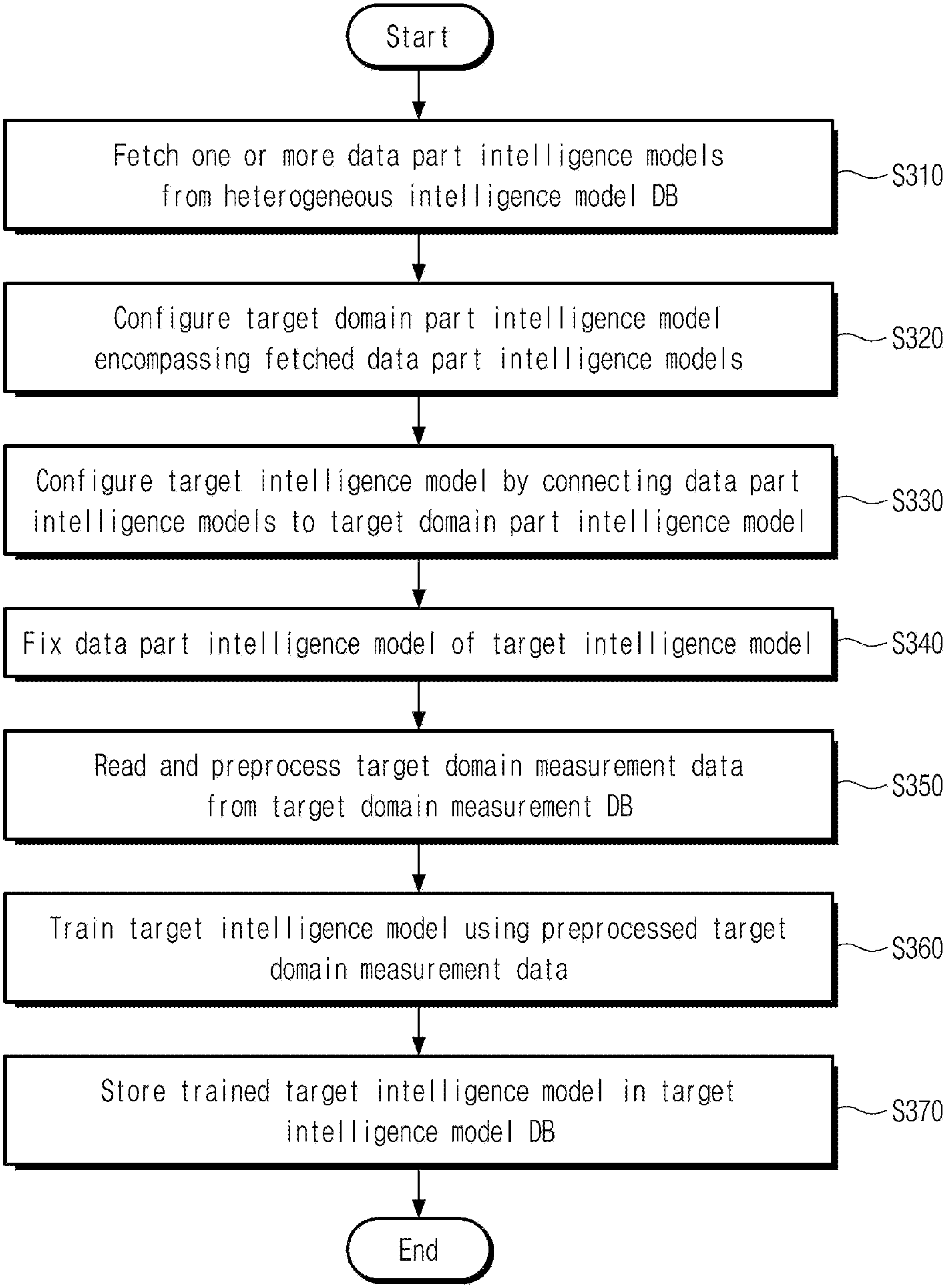
FIG. 5 is a flowchart illustrating an operation of a target intelligence model deep learning unit of FIG. 1.
Figure 6:
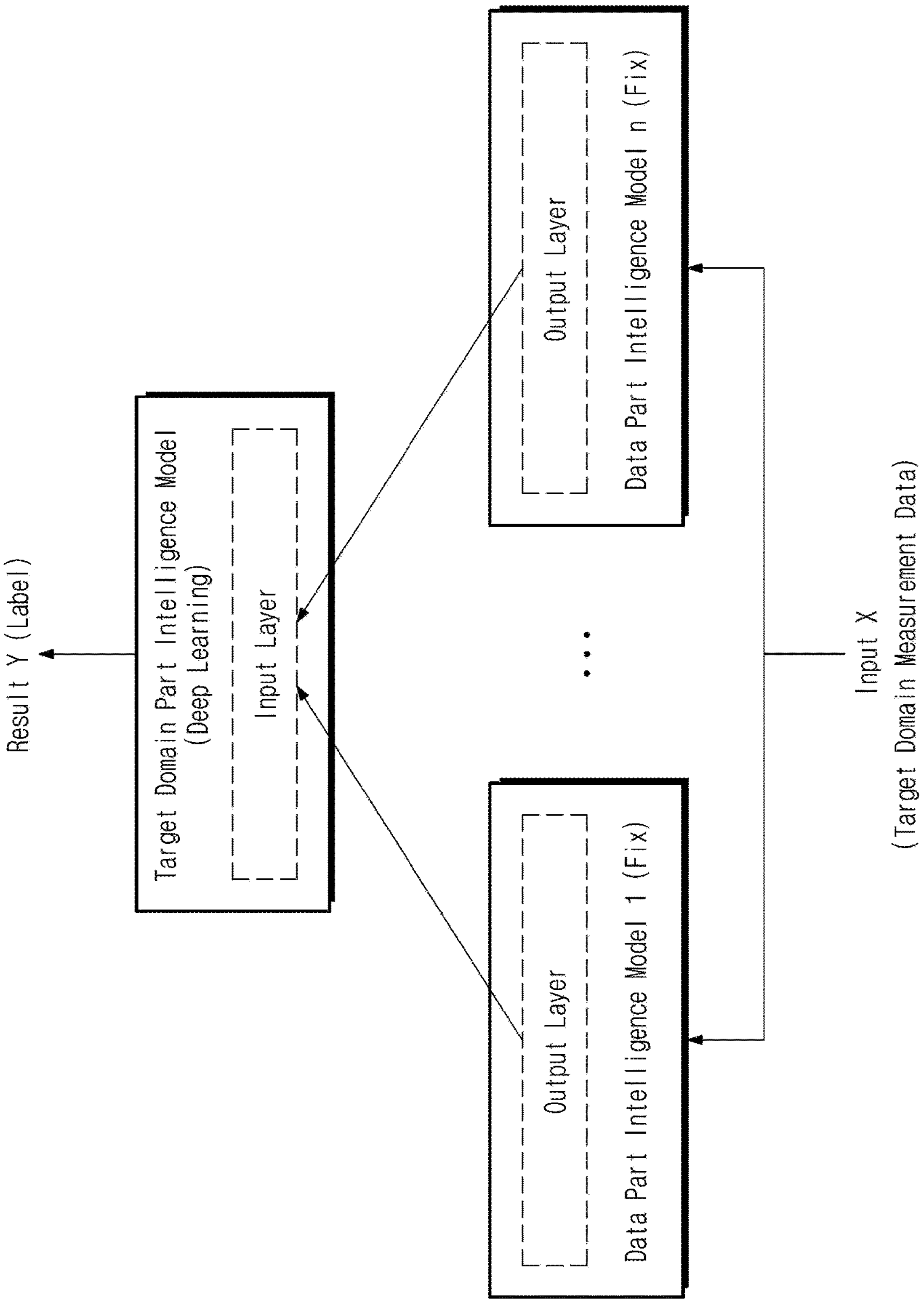
FIG. 6 illustrates a configuration of a heterogeneous intelligence model, according to an embodiment of the present disclosure.

FIG. 5 is a flowchart illustrating an operation of the target intelligence model deep learning unit 150 of FIG. 1, and FIG. 6 illustrates a configuration of a heterogeneous intelligence model, according to an embodiment of the present disclosure. The target intelligence model deep learning unit 150 may train the target intelligence model for detecting a target gas in a domain with few samples, and in this process, may use several heterogeneous data part intelligence models stored in the heterogeneous intelligence model DB 30, as described with reference to FIG. 3.

In operation S310, the target intelligence model deep learning unit 150 may fetch one or more data part intelligence models from the heterogeneous intelligence model DB 30. In operation S320, the target intelligence model deep learning unit 150 may configure a target domain part intelligence model that may encompass the fetched data part intelligence models (e.g., data part intelligence model '1' to data part intelligence model 'n'). Referring to FIG. 6, the target domain part intelligence model may have an input layer that may receive the results of the output layer of the data part intelligence models and an output layer that outputs the label "with target gas", and a hidden layer of the target domain part intelligence model may take various forms. Referring again to FIG. 5, in operation S330, the target intelligence model deep learning unit 150 may configure a target intelligence model by connecting the data part intelligence models to the target domain part intelligence model generated in operation S320. For example, in the case of target intelligence models, data part intelligence models may receive the target domain measurement data as the input X, and target domain part intelligence models may output a label (with target gas or absence of target gas) as the result Y.

In operation S340, the target intelligence model deep learning unit 150 may fix the data part intelligence model of the target intelligence model. The fixing ensures that the hidden layer variables of the data part intelligence model do not change during back-propagation during the training process of the intelligent model using deep learning, and this is because the target data part intelligence model is considered to be trained to some extent with heterogeneous data with similar properties. In operation S350, the target intelligence model deep learning unit 150 may read and preprocess the target domain measurement data from the target domain measurement DB 20. As described with reference to FIG. 3, preprocessing may include missing value processing, outlier removal, data normalization, etc.

In operation S360, the target intelligence model deep learning unit 150 may train the target intelligence model using the preprocessed target domain measurement data. In this case, since the data part intelligence model is fixed, only the target domain part intelligence model may be trained, and the target domain part intelligence model may be configured to have different complexity depending on the amount of data used for training. In operation S370, the target intelligence model deep learning unit 150 may store the trained target intelligence model in the target intelligence model DB 40.

Figure 7:
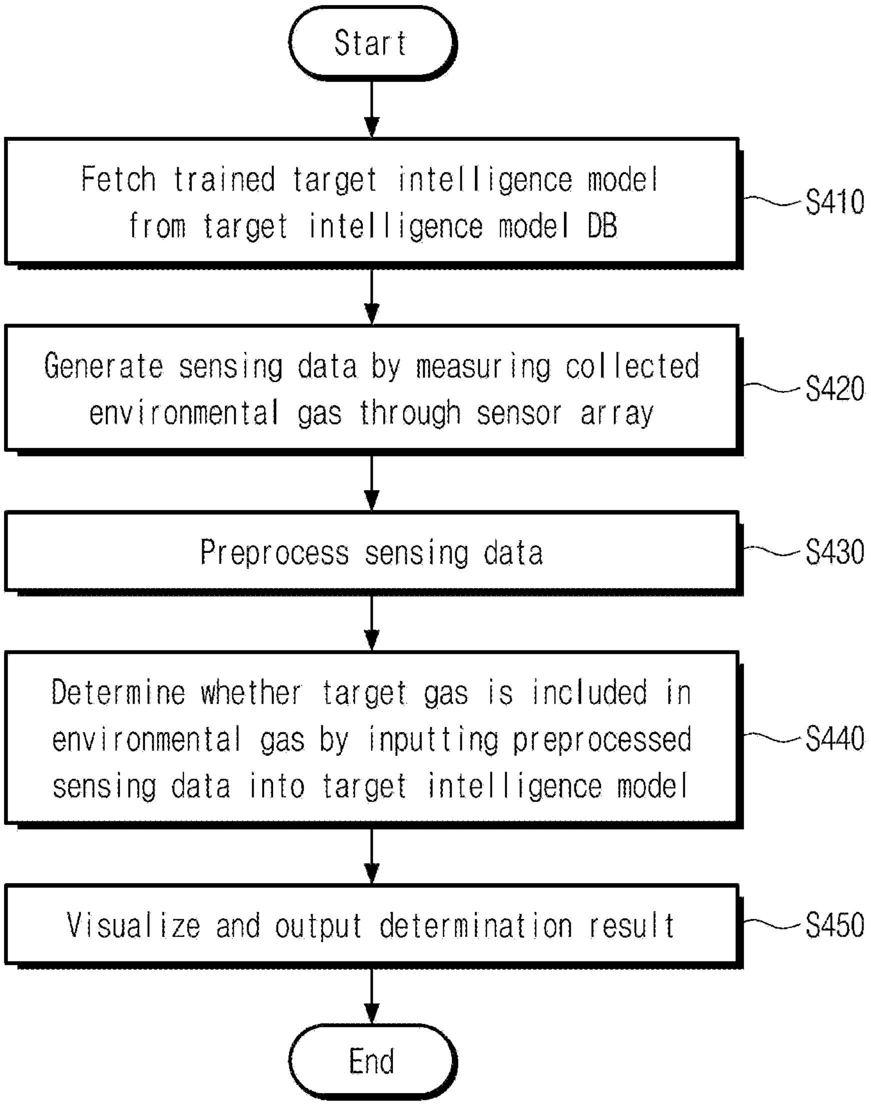
FIG. 7 is a flowchart illustrating an operation of a target gas detection unit of FIG. 1.

FIG. 7 is a flowchart illustrating an operation of the target gas detection unit 160 of FIG. 1. The target gas detection unit 160 may collect environmental gases in the actual domain and may detect whether the target gas is included in the collected environmental gases. Like the mixed gas measurement unit 130, the target gas detection unit 160 may include a sensor array.

In operation S410, the target gas detection unit 160 may fetch the trained target intelligence model from the target intelligence model DB 40. In operation S420, the target gas detection unit 160 may generate sensing data by measuring the collected environmental gas through the sensor array. The format of the sensing data is the same as that of the sensing data generated through the mixed gas measurement unit 130 described with reference to FIG. 2. In operation S430, the target gas detection unit 160 may preprocess the generated sensing data. For example, preprocessing of the sensing data may be performed in the same manner as operation S220 of FIG. 3 and operation S350 of FIG. 5. In operation S440, the target gas detection unit 160 may determine whether the target gas is included in the environmental gas by inputting the preprocessed sensing data into the target intelligence model. In operation S450, the target gas detection unit 160 may visualize and output the determination result.

Through the above-described embodiments, when the artificial intelligence apparatus 100 of the present disclosure is used, it is possible to train a target intelligence model that may effectively detect a target gas in a domain with few samples. In detail, the target intelligence model according to an embodiment of the present disclosure may be trained with only a small number of sample data, and the target intelligence model may be prevented from being overfitted even if the number of sample data is small. In addition, according to an embodiment of the present disclosure, the target intelligence model may be trained using data containing heterogeneous gases that are partly similar to the characteristics of the target gas. As a result, the heterogeneous intelligence models trained in advance may be applied to other domains, and the value of the target intelligence model may be improved.

According to an embodiment of the present disclosure, an artificial intelligence capable of detecting a target gas may be trained using only sample data from which a mixed gas is measured. In addition, overfitting problems may be prevented in a domain with a small number of samples.

Furthermore, according to an embodiment of the present disclosure, an artificial intelligence for target gas detection may be trained using data measured in a heterogeneous target gas domain that has partially similar characteristics to the target gas.

The above description refers to embodiments for implementing the present disclosure. Embodiments in which a design is changed simply or which are easily changed may be included in the present disclosure as well as an embodiment described above. In addition, technologies that are easily changed and implemented by using the above embodiments may be included in the present disclosure. While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. An artificial intelligence apparatus for detecting a target gas comprising:

a mixed gas measurement unit configured to measure a mixed gas collected in a plurality of domains through a sensor array to generate sensing data including heterogeneous domain measurement data measured from the mixed gas collected in a domain different from the target gas and target domain measurement data measured from the mixed gas collected from a same domain as the target gas;

a heterogeneous intelligence model deep learning unit configured to receive the heterogeneous domain measurement data to train a heterogeneous intelligence model;

a target intelligence model deep learning unit configured to receive the heterogeneous intelligence model and the target domain measurement data to train a target intelligence model; and a target gas detection unit configured to determine whether an environmental gas includes the target gas using the target intelligence model;

wherein the mixed gas measurement unit is configured to divide the collected mixed gas into a plurality of environmental gas bags, to distribute the target gas to a plurality of target gas bags according to a concentration, to generate a plurality of sample gas bags by mixing each of the environmental gas bags and each of the target gas bags, to set a measurement environment of the sensor array with respect to the sample gas bags, and to measure the mixed gas of each of the sample gas bags depending on the set measurement environment to generate the sensing data; and wherein the heterogeneous intelligence model and the target intelligence model are trained using a CNN (Convolutional Neural Network) and a ResNet.

2. The artificial intelligence apparatus of claim 1, wherein the measurement environment includes a measurement temperature, a gas pressure, and a sensor voltage.

3. The artificial intelligence apparatus of claim 1, wherein the heterogeneous intelligence model includes a data part intelligence model that trains the sensing data and a domain part intelligence model that trains a characteristic of a domain including the target gas, and wherein the heterogeneous intelligence model deep learning unit reads and preprocesses the heterogeneous domain measurement data, trains the heterogeneous intelligence model using the preprocessed heterogeneous domain measurement data, deletes the domain part intelligence model from the trained heterogeneous intelligence model, and stores only the data part intelligence model in a heterogeneous intelligence model database.

4. The artificial intelligence apparatus of claim 3, wherein the target intelligence model deep learning unit configures a target domain part intelligence model encompassing data part intelligence models fetched from the heterogeneous intelligence model database, connects the data part intelligence models and the target domain part intelligence model to configure the target intelligence model, fixes the data part intelligence models, reads and preprocesses the target domain measurement data, trains the target intelligence model using the preprocessed target domain measurement data, and stores the trained target intelligence model in a target intelligence model database.

5. The artificial intelligence apparatus of claim 1, wherein the sensing data is first sensing data, and wherein the target gas detection unit measures the environmental gas through the sensor array to generate second sensing data, preprocesses the second sensing data, determines whether the target gas is included in the environmental gas by inputting the preprocessed second sensing data into the target intelligence model, and visualizes and outputs a determined result.

6. A non-transitory computer-readable medium comprising a program code that, when executed by a processor, causes the processor to:

measure a mixed gas collected in a plurality of domains through a sensor array to generate sensing data including heterogeneous domain measurement data measured from the mixed gas collected in a domain different from the target gas and target domain measurement data measured from the mixed gas collected from a same domain as the target gas;

receive the heterogeneous domain measurement data to train a heterogeneous intelligence model;

receive the heterogeneous intelligence model and the target domain measurement data to train a target intelligence model; and determine whether an environmental gas includes the target gas using the target intelligence model;

wherein the generation of the sensing data includes:

dividing the collected mixed gas into a plurality of environmental gas bags;

distributing the target gas to a plurality of target gas bags according to a concentration;

generating a plurality of sample gas bags by mixing each of the environmental gas bags and each of the target gas bags;

setting a measurement environment of the sensor array with respect to the sample gas bags; and measuring the mixed gas of each of the sample gas bags depending on the set measurement environment to generate the sensing data; and wherein the heterogeneous intelligence model and the target intelligence model are trained using a CNN (Convolutional Neural Network) and a ResNet.

7. The non-transitory computer-readable medium of claim 6, wherein the heterogeneous intelligence model includes a data part intelligence model that trains the sensing data and a domain part intelligence model that trains a characteristic of a domain including the target gas, and wherein the training of the heterogeneous intelligence model includes:

reading and preprocessing the heterogeneous domain measurement data;

training the heterogeneous intelligence model using the preprocessed heterogeneous domain measurement data;

deleting the domain part intelligence model from the trained heterogeneous intelligence model; and storing only the data part intelligence model in a heterogeneous intelligence model database.

8. The non-transitory computer-readable medium of claim 7, wherein the training of the target intelligence model includes:

configuring a target domain part intelligence model encompassing data part intelligence models fetched from the heterogeneous intelligence model database;

connecting the data part intelligence models and the target domain part intelligence model to configure the target intelligence model;

fixing the data part intelligence models;

reading and preprocessing the target domain measurement data;

training the target intelligence model using the preprocessed target domain measurement data; and storing the trained target intelligence model in a target intelligence model database.

9. The non-transitory computer-readable medium of claim 6, wherein the sensing data is first sensing data, and wherein the determining of whether the environmental gas includes the target gas includes:

measuring the environmental gas through a sensor array to generate second sensing data;

preprocessing the second sensing data;

determining whether the target gas is included in the environmental gas by inputting the preprocessed second sensing data into the target intelligence model; and visualizing and outputting the determined result.

* * * * *